United States Patent [19]
Meriwether et al.

[11] Patent Number: 6,090,143
[45] Date of Patent: Jul. 18, 2000

[54] BOX CAGE FOR INTERVERTEBRAL BODY FUSION

[76] Inventors: Michael W. Meriwether, 2564 Tom Morris Dr.; Richard L. Shockey, 2679 Man of War Cir., both of Sarasota, Fla. 34240

[21] Appl. No.: 09/157,928

[22] Filed: Sep. 21, 1998

[51] Int. Cl.[7] .................................................... A61F 2/44
[52] U.S. Cl. ............................................................. 623/17
[58] Field of Search ................................ 623/17; 606/61

[56] References Cited

U.S. PATENT DOCUMENTS 5,888,228 3/1999 Kothe et al. .

OTHER PUBLICATIONS

Weiner, Bradley, et al., Spine, vol. 23, No. 5, pp. 634–640, "Spine Update Lumbar Interbody Cages" ©1998.
Ray, Charles, Neurosurgery Quarterly, vol. 7, No. 2, pp. 135–156, "Spinal Interbody Fusions: A Review, Featuring New Generation Techniques".
Ray, Charles, Spine, vol. 22, No. 6, pp. 681–685, Threaded Fusion Cages for Lumbar Interbody Fusions; An Economic Comparison with 360° Fusions.
Onesti, Stephen et al, Neurosurgery, vol. 42, No. 1, Jan. 1998 pp. 200–204 "Instrumentation, Techinque and Technology".

*Primary Examiner*—David J. Isabella
*Attorney, Agent, or Firm*—Nikolai, Mersereau & Dietz, P.A.

[57] ABSTRACT

An interbody implant for enhancing fusion of adjacent vertebral bodies comprises a rectangular cage member of an open construction dimensioned to fit between adjacent vertebral bodies following surgical removal of the disk. The rectangular cage member includes a plurality of ribs for engaging the plateaus of adjacent vertebral bodies for preventing lateral shifting of the cage. It is held against anterior/posterior motion by a locking screw which threadedly engages the cage and adjacent bone tissue. The cage is adapted to be packed with bone graft material for enhancing solid bone fusion.

17 Claims, 6 Drawing Sheets

BOX CAGE FOR INTERVERTEBRAL BODY FUSION

BACKGROUND OF THE INVENTION

I. Field of the Invention

This invention relates generally to apparatus for effecting intervertebral body arthrodesis, and more particularly to an improved cage construction for reducing movement of adjacent vertebral bodies to thereby enhance bone growth and fusion.

II. Discussion of the Prior Art

Intervertebral body arthrodesis or fusion of a spine segment is indicated for symptomatic patients with intervertebral disk disease. The purpose of the fusion in these cases is to eliminate or reduce the amount of motion at that site and, possibly, the source of pain. For solid bone fusion between vertebral bodies, it is imperative that interbody movement be prevented if bone growth and fusion is to result.

When a vertebral body or disk is damaged, the spinal cord or nerve roots may be impinged. This causes extreme pain to the person, either in the back, neck or extremities. When all conservative drug treatments and minimally invasive procedures have been exhausted. A spinal stabilization with fusion may be the answer. It has long been thought that interbody fusion achieves relief of the patient's pain by correction of an existing mechanical deformation to its anatomic baseline and by the provision of stability to the spine segment to prevent future abnormal, i.e., excessive or pain-provoking motions. Spinal interbody fusion has, in theory, been the preferred surgical technique to achieve these goals. Unfortunately, this procedure has demonstrated widely varying results, with fusion rates ranging from 19 percent to 95 percent and satisfactory clinical results ranging from 14 percent to 93 percent. Devices, referred to as "fusion cages" have been developed to help stabilize adjacent vertebral bodies to be fused and to help promote solid bone fusion between such vertebral bodies. Fusion cages have been designed to correct existing mechanical deformation, to provide stability to the vertebral bodies until arthrodesis is achieved, provide the best possible environment for successful arthrodesis and to achieve this with limited morbidity associated with their use.

Ideally, interbody cage devices should restore disk height, place the annular fibers in a "normal" tension, create lordosis through the joined vertebral bodies, obtain sagittal balance through the segment, reduce subluxed facet joints, enlarge the neuorforaminal space, and restore to normal the proportion of weight bearing through the anterial spinal column.

Presently, there are two types of cages, round and square. Such cages vary in size for the area of the spine in which they are to be implanted, i.e., lumbar, thoracic or cervical. FIG. 1 illustrates a typical prior art fusion cage, such as the so-called BAK cage available from SpineTech of Minneapolis, Minn., and the RAY threaded fusion cage from Surgical Dynamics of Norwalk, Conn. These cages are threaded titanium cylinders having a longitudinal bore extending through them and with holes through the walls of the cylinder located at the roots of the threads. The longitudinal bore can be packed with bone particles and the holes allow bony ingrowth through the cages during the post-operative healing phase.

Depending upon the location of the damaged disk, either one or two such cages may be implanted between adjacent vertebral bodies. Generally, in the lumbar region, two such cage devices are employed and they are positioned on either side of the mid-line sufficiently far apart that they do not touch one another and generally will be about 3 mm from the anterior and posterior cortical margin of the end plates comprising the vertebral body. The cylindrical cages come in several diameters and the diameter chosen again depends upon the anatomy of the spine at the point of placement.

In implanting such devices, semi-circular laminotomies are performed on both lateral sides of the disk space and then the bone of the plateaus of the adjacent vertebral bodies are drilled and tapped to receive the threaded cylinders therein. Before closure, autologous bone graft material, usually harvested from the patient's iliac crest is packed within the hollow confines of the cylindrical threaded cage devices to enhance the opportunity for solid bone fusion.

It is imperative for successful fusion that stability of the adjacent vertebral bodies be maintained as bone growth takes place, even when the patient has returned to his/her daily activities. Motion through the operative segments leads to progressive mechanical loosening and eventual failure of implant or bone. Motion significantly decreases the chances of obtaining a solid bony arthrodesis. While the RAY threaded fusion cage and the BAK fusion cage constitute an improvement over earlier intercorporeal bone graft in spinal fusion following disk removal, instances have been reported where the cylindrical threaded cages move out of position, especially if the patient's daily activities involve bending from side-to-side or front-to-rear. When the body leans forward, the disk between the vertebral bodies compress on the anterior side of the spinal column while the posterior disk stretches. When the body leans to the left, the left side of the disk compresses and the right side stretches. Just the opposite occurs when leaning to the right. When two cylindrical threaded cages are placed in between the vertebral bodies following removal of the disk therebetween, the compression and stretching of the disk is gone, but the vertebral bodies open slightly as explained above. With the radius of the cylindrical threaded cages, rotation can exist from side-to-side. When vertebral body can roll over the side of the cylindrical cage, but this will not happen on a forward or backward movement, because there is no radius curve over the length of the cage member. A need exists for a fusion cage design that prevents front-to-back and side-to-side shifting of the adjacent vertebral bodies as the patient bends or leans. An overview of cage devices presently in use for interbody fusion are set forth in an article entitled "Spine Update—Lumbar Interbody Cages", by Bradley K. Weiner, M.D., *Spine,* Vol. 23, No. 5, Mar. 1, 1998, pp. 634–640.

SUMMARY OF THE INVENTION

In accordance with the present invention, there is provided an interbody implant for enhancing fusion of adjacent vertebral bodies that comprises a rectangular, box-like cage member having four mutually perpendicular sidewalls of a predetermined height dimension, allowing insertion between adjacent vertebral bodies. Extending between an opposed pair of the four sidewalls are a plurality of parallel, spaced-apart rib members. This opposed pair of sidewalls also include an aperture therethrough of a predetermined diameter.

Completing the device is a locking screw with threads of a predetermined pitch and a length dimension that allows threaded insertion into said apertures. The locking screw has a root diameter that is less than the predetermined diameter of the apertures formed through the opposed pair of sidewalls and a crest diameter that is greater than the predetermined height dimension of said opposed pair of sidewalls.

Being so designed, the locking screw is adapted to threadingly engage tapped rounded grooves surgically created in the adjacent vertebral bodies when the cage member is inserted between the adjacent vertebral bodies and the locking screw is threaded into the apertures in the opposed pair of sidewalls. The locking screw prevents anterior/posterior displacement of the rectangular cage member while the plurality of parallel, spaced-apart rib members engage the adjacent vertebral bodies to prevent lateral shifting of the cage member with bending or leaning following insertion into the intervertebral space.

DESCRIPTION OF THE DRAWINGS

The foregoing features, objects and advantages of the present invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
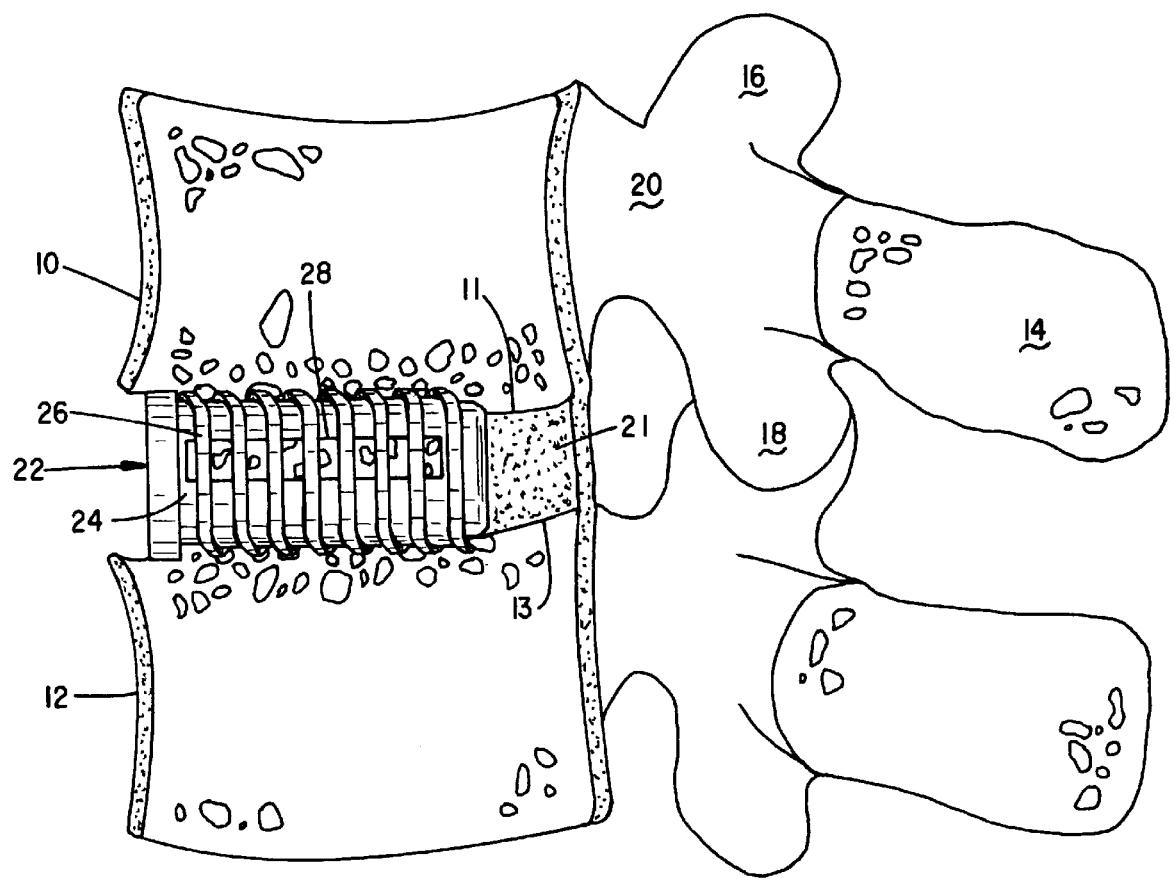
FIG. 1 illustrates a prior art threaded, cylindrical fusion cage positioned in the interbody space between two vertebral bodies.

With reference to FIG. 1, there is shown a cross-sectional view through two adjacent vertebral bodies 10 and 12 and shown for references purposes is the spinous process 14, the superior articular process 16, the inferior articular process 18 and the pedicle 20 of the vertebral bodies.

While not shown in FIG. 1, between adjacent vertebral bodies lies the intervertebral disk. The disk is comprised of two parts, namely a central part, called the nucleus, which is a gelatinous substance that is generally transparent and comprises approximately 88 percent water. Surrounding the nucleus is a peripheral part called the annulus, which is made of concentric fibers. They enclose the nucleus in an inextensible casing, holding it under pressure to prevent prolapse. The nucleus of the disc normally acts as a spherical swivel joint, allowing tilting in the sagittal plane, flexion and extension tilting in the frontal plane as well as lateral flexion. The nucleus further permits rotation whereby one vertebra can swivel relative to another. Limited gliding movement of one vertebral body over another is also allowed for by the nucleus.

Spinal injury due to compression loads or over-extension may injure the disk resulting in a bulging of the nucleus beyond the annulus which often results in impingement of nucleus material on nerve structures, resulting in chronic pain. Where drugs or other less aggressive surgical procedures fail to alleviate the condition, a procedure known as spinal bone fusion may be in order. In this procedure, the affected disk is removed and means are provided for grafting bone between the adjacent vertebral bodies so that a rigid union of those vertebral bodies results.

Prior art techniques in achieving intervertebral fusion have involved the insertion of small pieces of bone, usually harvested from the pelvic bone, in the intervertebral space. Over time, the bone fragments grow into one unit. It is found, however, that movement at the location of the graft often prevents successful fusion and resulting stability.

To help stabilize the vertebral bodies 10 and 12 as the graft material 20 solidifies, a prior art cylindrical threaded cage device 22 may be surgically implanted. The cage device 22 comprises a cylindrical hollow screw body 24 having threads 26 formed thereon. Formed through the cylindrical screw device 22 at the root of the threads are a plurality of openings, as at 28, that are equally circumferentially spaced. During the surgical insertion thereof, a drill and tap are used to form threads in the facing surfaces of the vertebral bodies 10 and 12, allowing the screw or cage 22 to be threaded into the prepared opening. Depending upon the location in the spinal column where the injury is located, either a single such screw or a pair of screws are inserted into the intervertebral space on opposite sides of the midline thereof to stabilize the vertebral bodies against motion. Bone chips or bone graft material is then packed within the hollow center of the screw.

While prior art cylindrical cages inhibit gliding movement of vertebral body 10 relative to vertebral body 12, tilting by way of lateral flexion and tilting in the sagittal plane can still result which necessarily impedes the formation of solid bone fusion. Leaning from side-to-side may also result in a slight rotational movement of the vertebral bodies over the cylindrical (rounded) surface of the cylindrical cages.

Figure 2:
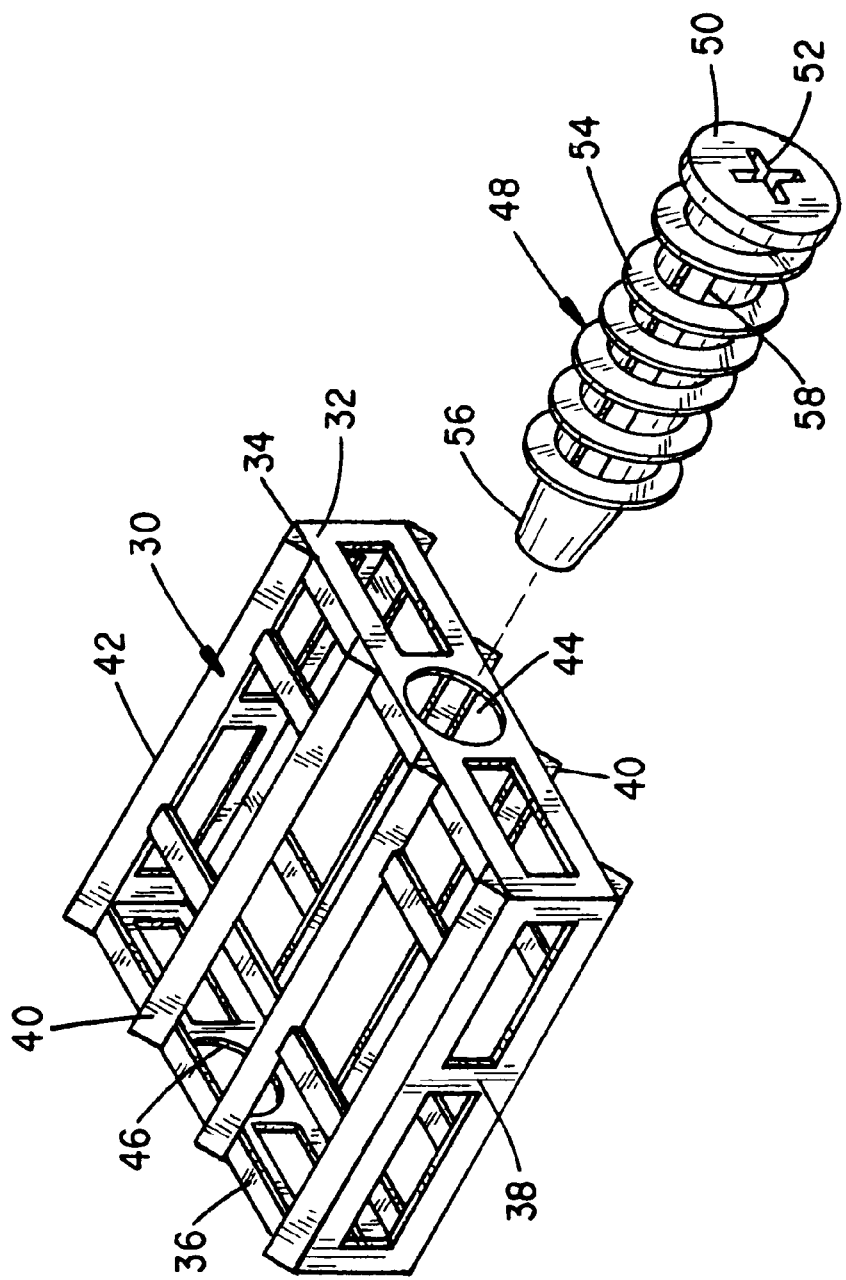
FIG. 2 is an exploded perspective view of the box cage device comprising a preferred embodiment of the invention.

To obviate this problem, in accordance with the present invention, and as illustrated in the exploded view of FIG. 2, there is provided a generally rectangular box-like cage member, indicated generally by numeral 30, having four mutually perpendicular sidewalls 32, 34, 36 and 38 of a predetermined height dimension, allowing insertion between adjacent vertebral bodies using either an anterior, a posterior or a lateral approach. Extending between opposed sidewalls 32 and 36 are a plurality of parallel, spaced-apart rib members 40. The rib members are preferably triangular in shape as illustrated terminating in a ridge line 42.

The opposed side edges 32 and 36 also each include a circular aperture, as at 44 and 46, for receiving therein a locking screw member indicated generally by numeral 48. The locking screw 48 includes a head 50 having a non-circular recess 52 formed inwardly of a face surface thereof for receiving an appropriate screw driver-like tool. The locking screw has a raised thread 54 of a predetermined pitch slightly wider than the thickness dimension of the end walls 32 and 36. The root diameter of the locking screw 48 allows it to be fitted through the aperture 44 and advanced until the tapered end portion 56 thereof passes into the aperture 46 of the sidewall 36. The crest diameter of the locking screw 48 is made greater than the height dimension of the mutually perpendicular sidewalls 32, 34, 36 and 38 of the cage member 30, and, as such, the threads project outwardly beyond the level of the edges of the side walls.

As in the case of the prior art RAY and BAK cages, the hollow interior of the locking screw 48 may be packed with bone chips and a plurality of openings, as at 58, are formed at the root of the threads leading to the hollow interior.

Figure 3:
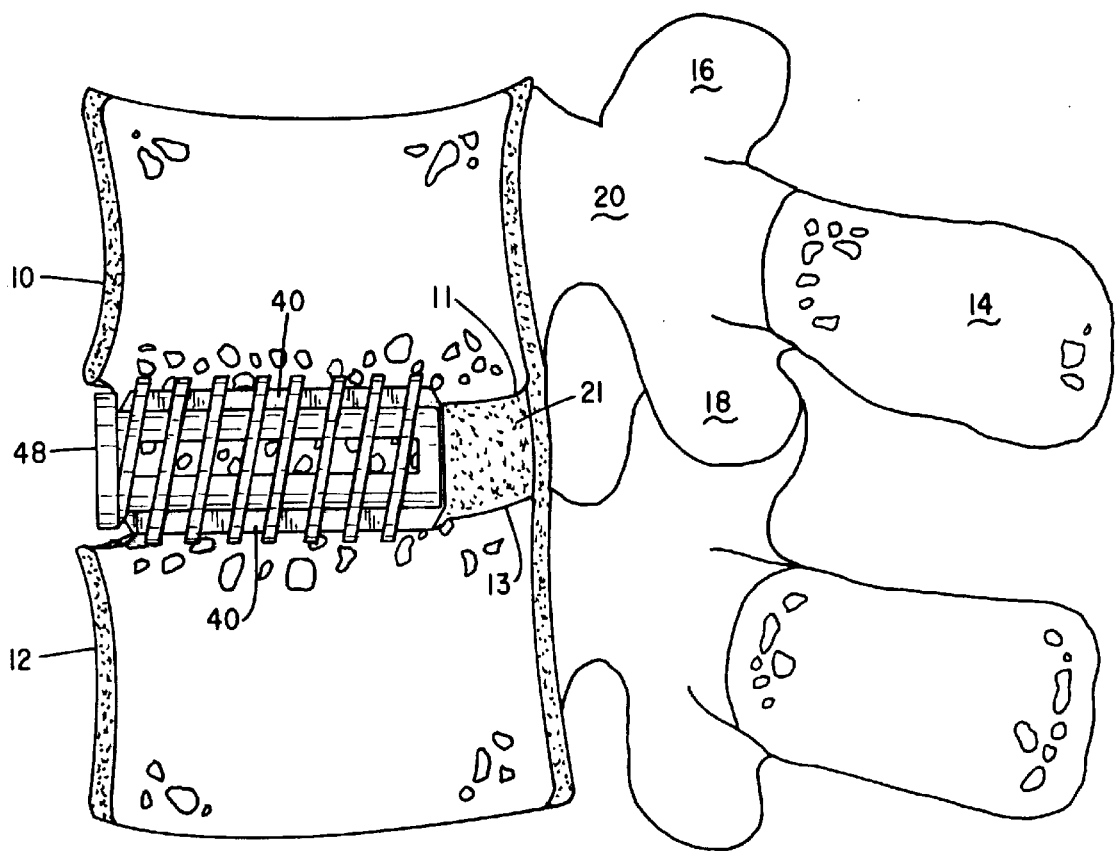
FIG. 3 is a side sectional view through two vertebrae of the spine and showing the device of FIG. 2 in the intervertebral space.

Referring next to FIG. 3, the rectangular, box-like cage member 30 is shown in its surgically implanted position between vertebral bodies 10 and 12 following a disectomy procedure to remove the damaged disk. The height dimension of the sidewalls, as well as their length dimension, are selected based upon the anatomy of the spinal column at the surgical site. The sidewalls of a cage member designed for placement between lumbar vertebral members may be in a range of from 10 mm to 18 mm, whereas a cage being placed in the cervical region may have a height dimension in a range of from 4 mm to 10 mm. Using an anterior approach, the cage 30 is driven into position using a hammer instrument. As the cage member 30 is advanced into the intervertebral space, the exposed sharp edges 42 of the ribs 40 dig into the bone surfaces of the plateaus 11 and 13 of the respective vertebral bodies 10 and 12. These ribs prevent lateral displacement of the cage 30. To inhibit movement interiorly and posteriorly, the locking screw 48 is threadedly advanced into the apertures 44 and 46 of the cage member 30. The crests of the threads on the locking screw 48 are designed to engage corresponding threads surgically formed in the plateaus 11 and 13 using a drill and tap. It will be recalled that the crest diameter of the locking screw is greater than the height dimension of the mutually perpendicular sidewalls such that the threads can engage the bone material, locking the cage device in position.

In that the cage member 30 has a generally open construction, including fenestrated sidewalls, it too can be packed with bone graft material which ultimately matures into a solid bony connection between the now-fused vertebral bodies. Because of the greater width dimension of the preferred embodiment as compared to the size of the prior art RAY and BAK cages, the adjacent vertebral bodies are precluded from movement as the patient leans to one side or the other or bends forward and backward. The greater stability afforded to the vertebral bodies enhances the ability for bone fusion to take place.

Figure 4:
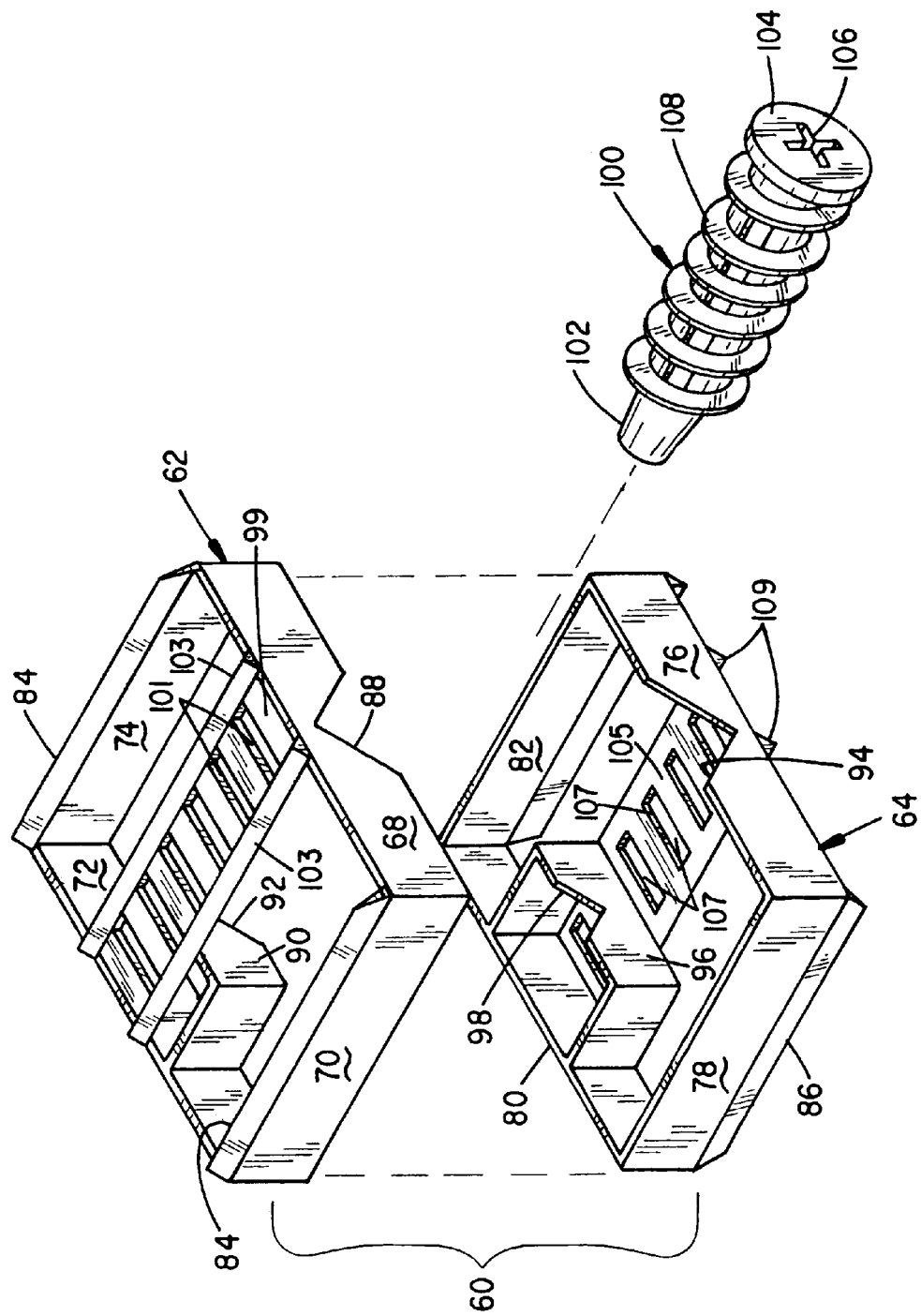
FIG. 4 is an exploded perspective view of the alternative preferred embodiment of the invention.

Referring now to the exploded view of FIG. 4, there is shown an alternative embodiment of the present invention that permits limited adjustment of the height dimension of the cage member. Here, the cage member 60 comprises first and second halves 62 and 64, each having four mutually perpendicular sidewalls, as at 68–74 for cage half 62 and 76–82 for cage half 64. The length and width of the sidewalls of cage half 62 are slightly larger than the corresponding dimensions of the cage half 64 whereby the cage half 62 will fit over the cage half 64 like the cover on a shirt box. Extending between opposed sidewalls 68 and 72 of the cage half 62 are a plurality of ribs as at 84. Likewise, the second cage half 64 also includes a plurality of rib members 86 extending between opposed side edges 76 and 80 proximate the lower edge thereof.

The side edge 68 includes a V-shaped notch 88 extending through the thickness dimension thereof. Formed internally and affixed to the opposed side edge 72 is an inwardly projecting boss 90, also having a V-shaped notch 92 formed therein and aligned with the notch 88. In a similar fashion, the side edge 76 of the lower box half 64 includes a V-shaped notch 94. An inwardly projecting boss 96 on the box half 64 includes a similar V-shaped notch 98. Extending longitudinally between end wall 68 and 72 of the upper cage half 62 is a plate 99 having a series of regularly spaced, transversely extending notches 101 formed through the thickness dimension thereof. Running along the side edges of the elongated plate 99 are triangular ribs 103. Similarly, spanning the box half 64 is a plate 105 having regularly spaced slots 107 formed therethrough triangular, downwardly projecting ribs 109 extend along the side edges of the plate 105.

The upper and lower cage halves may be fabricated from a suitable metal or plastic with titanium being presently preferred because of its strength and lightweight properties.

Completing the assembly is a locking screw 100. It is of a generally uniform diameter over a majority of its length, but it tapers to a lesser diameter at an end 102 thereof. The screw 100 has a head 104 with a tool receiving notch 106 formed therein. The threads 108 on the locking screw 100 are of a predetermined pitch and have a crest diameter which is greater than the thickness dimension of the sidewalls 68 and 76. The pitch is such that the threads extend through the slots 101 and 107 of the plate members 99 and 105.

Figure 5:
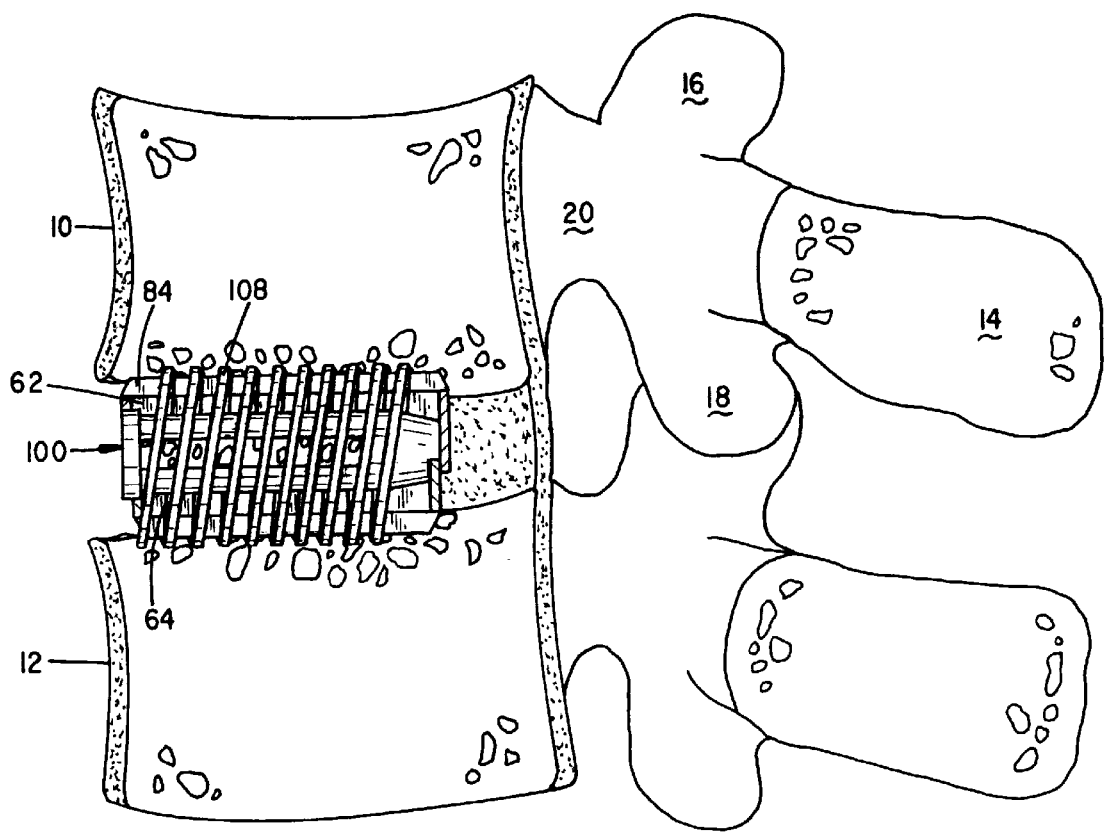
FIG. 5 is a side cross-sectional view like that of FIG. 3, but with the alternative preferred embodiment of FIG. 4 inserted.

Referring now to FIG. 5, there is shown a vertical cross-section through the vertebral members 10 and 12 with the box cage of the embodiment of FIG. 4 disposed in the intervertebral space. Once the box halves 62 and 64 have been inserted into the intervertebral space, a locking screw 100 of a preselected diameter is advanced into the opening formed by the overlapping V-shaped notches 88 and 94 until the tapered distal end 102 thereof falls into the opening defined by the overlapping notches 92 and 98. Continued advancement of the locking screw 100 will cause the cage halves 62 and 64 to spread apart relative to one another, thereby pressing the ribs 84, 86, 103 and 109 into the bone comprising the facing plateaus of the vertebral bodies 10 and 12. The degree of spreading of the box halves relative to one another is controlled by the selection of the root diameter of the locking screw 100. Because the threads are designed to be deep enough to allow the thread crests to project through the regularly spaced slots 101 and 107 in the plate members 99 and 105, they can penetrate into bone tissue of the plateaus of the adjacent vertebral bodies to inhibit displacement anteriorly and posteriorly.

Figure 6:
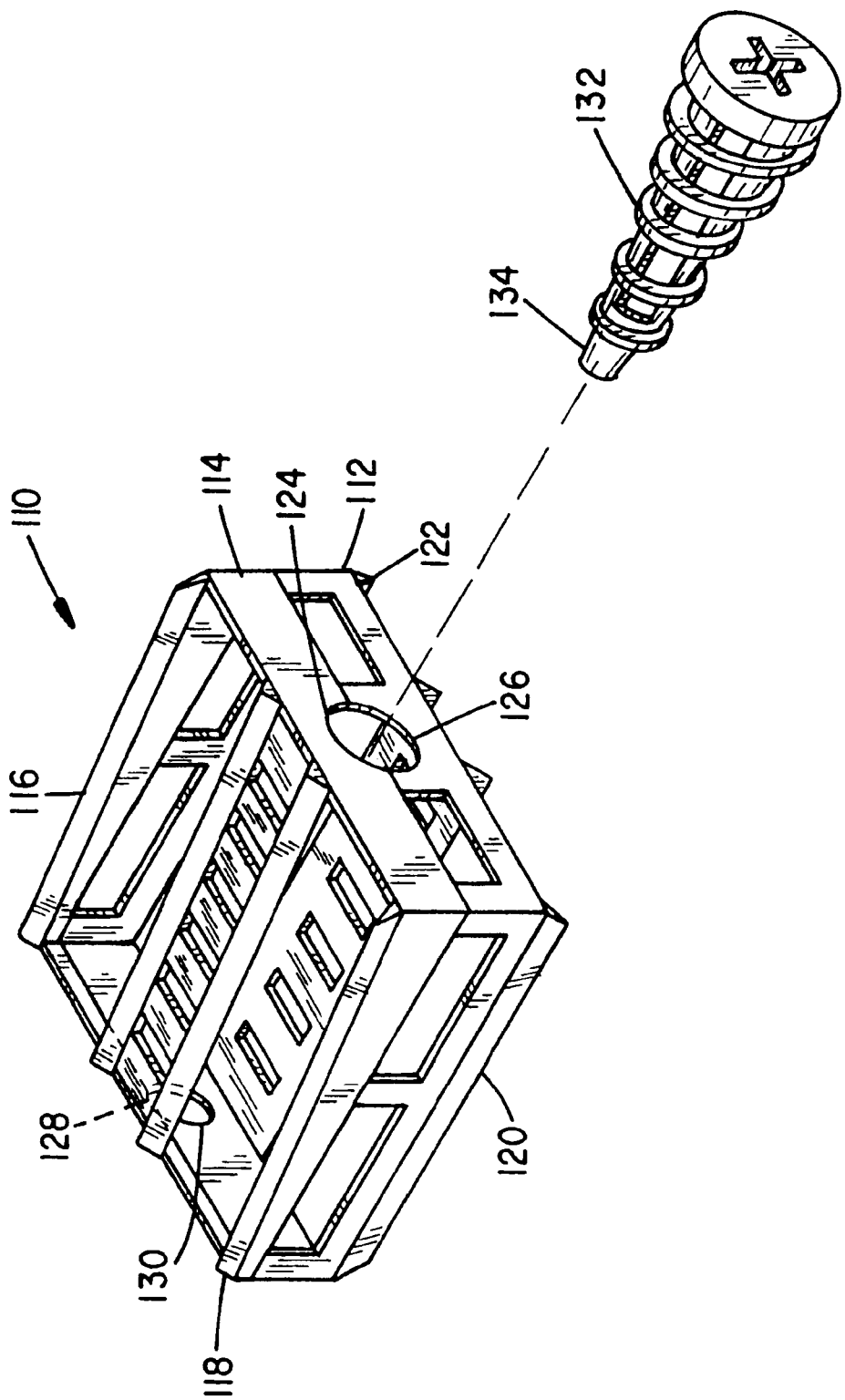
FIG. 6 is a perspective view of another alternative embodiment of the invention.

FIG. 6 illustrates a further embodiment of the invention which is a slight modification of that shown in FIG. 4. In the embodiment of FIG. 6, rather than having a rectangular longitudinal cross-section, it is trapezoidal such that the resulting cage member, indicated generally by numeral 110, is wedge-shaped. The assembled cage comprises a box-like base 112 and a cover 114 dimensioned to fit over the base much like the cover on a shirt box. The height dimension of the rightmost ends of the base and cover are greater than the height dimension of the corresponding, opposed left side ends, thus providing the desired wedge shape. Upwardly projecting ribs 116 and 118 extend along the rear and front side edges, respectfully, and likewise, the base 112 includes longitudinally extending ribs 120 and 122 projecting downwardly from the undersurface of the base along the side edges thereof. The right and left ends of the base 112 and the cover 114 include semi-circular cut-outs as at 124 and 126 and 128–130 such that when the cover 114 is placed upon the base 112, circular apertures are formed. These apertures are adapted to receive a tapered screw 132 therein. The slope of the taper of the screw is designed to correspond to that of the cage assembly 110 such that when the screw 132 is threaded into the circular opening defined by arcuate cut-outs 124 and 126 and advanced by turning until the leading end 134 of the screw enters the circular aperture 128–130, further turning of the screw will raise the case cover 114 relative to its base 112, allowing adjustment of the cage height following positioning thereof between adjacent vertebral bodies.

Again, the screw 132 is designed to have a relatively deep thread such that the periphery of the threads will project outward from the top of the cover 114 and the bottom of the base 112 so as to threadingly engage bone tissue of the plateaus of the adjacent vertebral bodies.

Thus, as in the embodiment of FIG. 4, the triangular ribs 116, 118, 120 and 122 are adapted to dig into bone tissue to prevent lateral shifting of the cage between their adjacent vertebral bodies while the threaded screw 132 when advanced through the cage prevents anterior-posterior movement of the cage. The cage is again of an open construction, allowing it to be packed with bone particles for enhancing the fusion process. The stability afforded by the wedge-shaped cage construction enhances the likelihood of a successful fusion.

The rectangular cage members 30 (FIG. 2) and 60 (FIG. 4) are preferably fabricated from a body compatible material, such as stainless steel, titanium, carbon, alloy composites and combinations thereof. Likewise, the locking screw can also be formed from these materials with titanium, perhaps, being preferred. Electronic discharge machining techniques may be used to form the window openings in the side walls of the cage as well as the openings formed inwardly to the hollow center of the locking screws at the roots of the threads.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An interbody implant for enhancing fusion of adjacent vertebral bodies comprising:
   (a) a cage member of generally rectangular cross-section having four mutually perpendicular sidewalls of predetermined height dimension, allowing insertion between adjacent vertebral bodies, and a plurality of parallel, spaced-apart rib members extending between an opposed pair of said four sidewalls, each of said opposed pair of sidewalls including an aperture therethrough of a predetermined diameter; and
   (b) a locking screw with threads of a predetermined pitch and a length allowing threaded insertion into said apertures, the locking screw having a root diameter less than said predetermined diameter and a crest diameter greater than the predetermined height dimension of the opposed pair of sidewalls and adapted to threadingly engage the adjacent vertebral bodies when the cage member is inserted between the adjacent bodies and the locking screw is threaded into the apertures in the opposed pair of sidewalls.

2. The interbody implant of claim 1 wherein the plurality of spaced apart rib members project outwardly above and below the opposed pair of sidewalls and adapted to engage the adjacent vertebral bodies for inhibiting lateral displacement of the cage member following implant.

3. The interbody implant of claim 1 wherein the locking screw includes a longitudinal bore and openings of a predetermined size are formed through the locking screw at the roots of said threads for permitting bone growth therethrough.

4. The interbody implant of any one of claims 1–3 wherein the cage member is formed of a material selected from a class consisting of stainless steel, titanium carbon, alloy composites and combinations thereof.

5. The interbody implant of claim 1 wherein the cage member comprises:
   (a) first and second cage halves, each having four mutually perpendicular sidewalls of a predetermined height dimension and a plurality of parallel, spaced-apart ribs extending between an opposed pair of sidewalls on each of the first and second halves and with the length and width dimension of the four mutually perpendicular side walls of each of the first and second cage halves being such that the first cage half will fit within the second cage half.

6. The interbody implant as in claim 5 wherein the threaded insertion of the locking screw into the apertures spreads the first and second cage halves apart from one another for altering the effective height dimension of the cage member.

7. The interbody implant of claim 5 wherein the plurality of spaced apart rib members project outwardly above and below the opposed pair of sidewalls and adapted to engage the adjacent vertebral bodies for inhibiting lateral displacement of the cage member following implant.

8. The interbody implant of claim 5 wherein the locking screw includes a longitudinal bore and openings of a predetermined size are formed through the locking screw at the roots of said threads for permitting bone growth therethrough.

9. The interbody implant of any one of claims 5–8 wherein the first and second cage halves are formed of a material selected from a class consisting of stainless steel, titanium carbon, alloy composites and combinations thereof.

10. The interbody implant of claim 1 wherein predetermined ones of the four mutually perpendicular sidewalls include openings formed through a thickness dimension thereof.

11. The interbody implant of claim 5 wherein predetermined ones of the four mutually perpendicular sidewalls include openings formed through a thickness dimension thereof.

12. The interbody implant of claim 1 wherein the cage member comprises:
   (a) first and second cage halves, each having a pair of side walls held in parallel spaced relation by a pair of parallel, spaced-apart end walls with the end walls being of a different height dimension, the first cage half having length and width dimensions greater than corresponding dimensions of the second cage half allowing the second cage half to fit within the first cage half and providing a wedge shape to the cage.

13. The interbody implant as in claim 12 wherein the threaded insertion of the locking screw into the apertures spreads the first and second cage halves apart from one another for altering the effective height dimension of the cage member.

14. The interbody implant as in claim 13 wherein the locking screw is frusto-conical in shape.

15. An interbody implant for enhancing fusion of adjacent vertebral bodies comprising:
   (a) a cage member having opposed parallel spaced apart front and rear faces and side faces, a generally rectangular cross-section and an open construction, the cage member dimensioned to fit between adjacent vertebral bodies upon surgical removal of an intermediate disk, the cage member including means adapted to engage bone tissue of plateaus of said adjacent vertebral bodies for preventing lateral displacement of the cage member;
   (b) an aperture centrally disposed in the front and rear faces; and (c) a locking screw adapted to be threadedly advanced through the aperture in the front face of the cage member and said bone tissue of said plateaus and into the aperture in the rear face for preventing anterior/posterior displacement of the cage member.

16. The interbody implant of claim 15 wherein the locking screw has a thread root diameter and a thread crest diameter where the thread root diameter is less than a diameter of the aperture and the crest diameter is greater than a height dimension of the cage member.

17. The interbody implant of claim 16 wherein the locking screw is tubular with a longitudinally extending lumen and includes a plurality of apertures extending from the root diameter to the lumen.

* * * * *